United States Patent [19]

Strohsahl

[11] Patent Number: Plant 6,149

[45] Date of Patent: Apr. 12, 1988

[54] JUNIPER BORLYN

[75] Inventor: Lynn J. Strohsahl, San Clemente, Calif.

[73] Assignee: Bordier's Nursery, Inc., Irvine, Calif.

[21] Appl. No.: 762,267

[22] Filed: Aug. 5, 1985

[51] Int. Cl.[4] ..... A01H 5/00

[52] U.S. Cl. ..... Plt./50

[58] Field of Search ..... Plt./50

[56] References Cited

U.S. PATENT DOCUMENTS

P.P. 2,491 4/1965 Sakiyama ..... Plt. 50

P.P. 5,014 3/1983 Girard ..... Plt. 50

*Primary Examiner*—James R. Feyrer

*Attorney, Agent, or Firm*—G. Donald Weber, Jr.

[57] ABSTRACT

'Borlyn' differs from its parent 'Old Gold' and other related varieties primarily in having more yellow-gold coloration which is less seasonally affected.

3 Drawing Sheets

This invention relates to a new and distinct variety of ornamental evergreen plant of the species *Juniperus chinensis*.

The outstanding and distinguishing characteristics of this new variety of plant are the vivid color, which changes slightly with colder weather. The bright golden yellow color dominates the plant so as to give the appearance of a golden cushion with the green leaves substantially hidden underneath. The yellow color tends to dominate all branches which receive full sun. Even when the branches are turned over, the yellow on the upper areas extends beyond the green areas or leaves.

The plant exhibits a relatively fast and vigorous growth to a width of approximately six (6) feet and a height of approximately three (3) feet but maintains its natural compactness of body with little trimming. The plant has a broad, full, well-filled shape which maintains its color and vitality and grows close to the ground.

This unique and distinct coloring is constant, and has been observed on all plants grown from cuttings taken for a period of several years. More than one thousand three hundred (1300) plants have been asexually reproduced since the discovery of the original and all retain the superior qualities enumerated above, while the noted coloring is always present.

This plant originated as a sport of the species *Juniperus chinensis* "Old Gold". It was found growing as a whole plant among a bed of cultivated "Old Gold" Junipers in Orange County, Calif. All plants have the same uniform growth and colors mentioned above.

The new variety is disclosed in the accompanying color photographic illustrations, in which:

FIG. 1 is a photograph of an actual evergreen plant which illustrates the general shape and color of the plant FIG. 2 is another photograph of the actual plant and illustrates the shape, color and compactness of the plant FIG. 3 is a photograph of a portion of the specimen depicted in FIG. 1 and illustrates the color, especially at the ends of the branches.

The coloring in the photographs is approximately natural insofar as it is possible to reproduce.

The foliage extending outwardly from brown-green branches is substantially the same texture and size of evergreen plants of *Juniperus chinensis* but the compact growth and full base and body present a more solid appearance throughout all seasons. The leaves tend to be relatively flat and alternate, while the branches tend to spread. The yellow color is carried approximately 10 to 12 inches from the tips of the branches. The leaves also tend to be relatively softer and longer than the leaves of the "Old Gold" plant.

The plant illustrated is one of over four hundred (400) growing in five gallon containers. All plants have the same uniform growth and color as mentioned and hereafter claimed. The temperature range for this shrub should be the same as its parent, viz. Zone 5 of the U.S.D.A. hardiness map or −20° to +110° F. The color is only slightly affected by changes in temperature. Rain, snow or other elements do not appear to alter the appearance or growth of the plants.

More specifically, this new variety of evergreen plant is described as follows, color designations being as found in "The Royal Horticulture Colour Chart."

General characteristics: Spreading; dense; compact; hardy; relatively fast growing.

Colors: 143C Scheeles Green to 10A Barium Yellow.

Trunk: Crooked; smooth surface texture; color — 200A.

Branches: Spreading or arching outward; color — 200D.

Leaves: Scale-leaves acute; needle-leaves acute; both entire.

Flowers: None observed to date.

The following chart gives a comparison of the most distinguishing characteristics of the parent plant 'Old Gold' and the plant 'Borlyn':

| 'OLD GOLD' | 'Borlyn' |
|---|---|
| Plant grows rounder<br>Width = 5'<br>Heighth = 3'<br>Vigor = Slow growing | Plant grows flatter<br>Width = 6'<br>Heighth = 3'<br>Vigor = Faster and more vigorous |
| Coloration = There is less yellow foliage. Therefore, green is more apparent. In turning branches over, little if any yellow is noticed. Yellow and green are mixed even if full sun. The yellow is carried 3–6" along the branch. | Coloration = Because there is so much yellow on top, the green is hidden underneath. In turning branches over, the yellow on the upper areas extends beyond the green. The yellow is more |

-continued

| 'OLD GOLD' | 'Borlyn' |
|---|---|
| | dominant on all branches in full sun. The yellow is carried 10–12" along the branches. |
| Yellow leaves 153 D - (pale white-yellow) | Yellow leaves 10 A - (deep golden yellow) |
| Green leaves 138 B | Green leaves 143 C |
| Branching = open and spiney | Branching = fine and lacey |
| Leaf characteristics = Leaves alternate and branches are fuller. Leaves are stiffer and more compressed. | Leaf characteristics = Leaves are flatter and alternate. Branches are spreading. Leaves are softer and longer |

Having thus described the invention, what I claim as new and desire to secure by Letters Patent is:

1. The new and distinct variety of evergreen plant as described and illustrated, characterized by its relatively fast growth and its foliage being predominantly golden yellow in color at the tips thereof and extending along the branches thereof, and ranging to a relatively dark green near the zone of juncture with the supporting branches, giving the entire plant a bright color throughout its body with a relatively fine, lacy and dense growth habit; its ability to withstand temperature changes with only slight alteration in color; its compact body and broad full base growing very close to the ground and remaining vital and true as to color throughout said base.

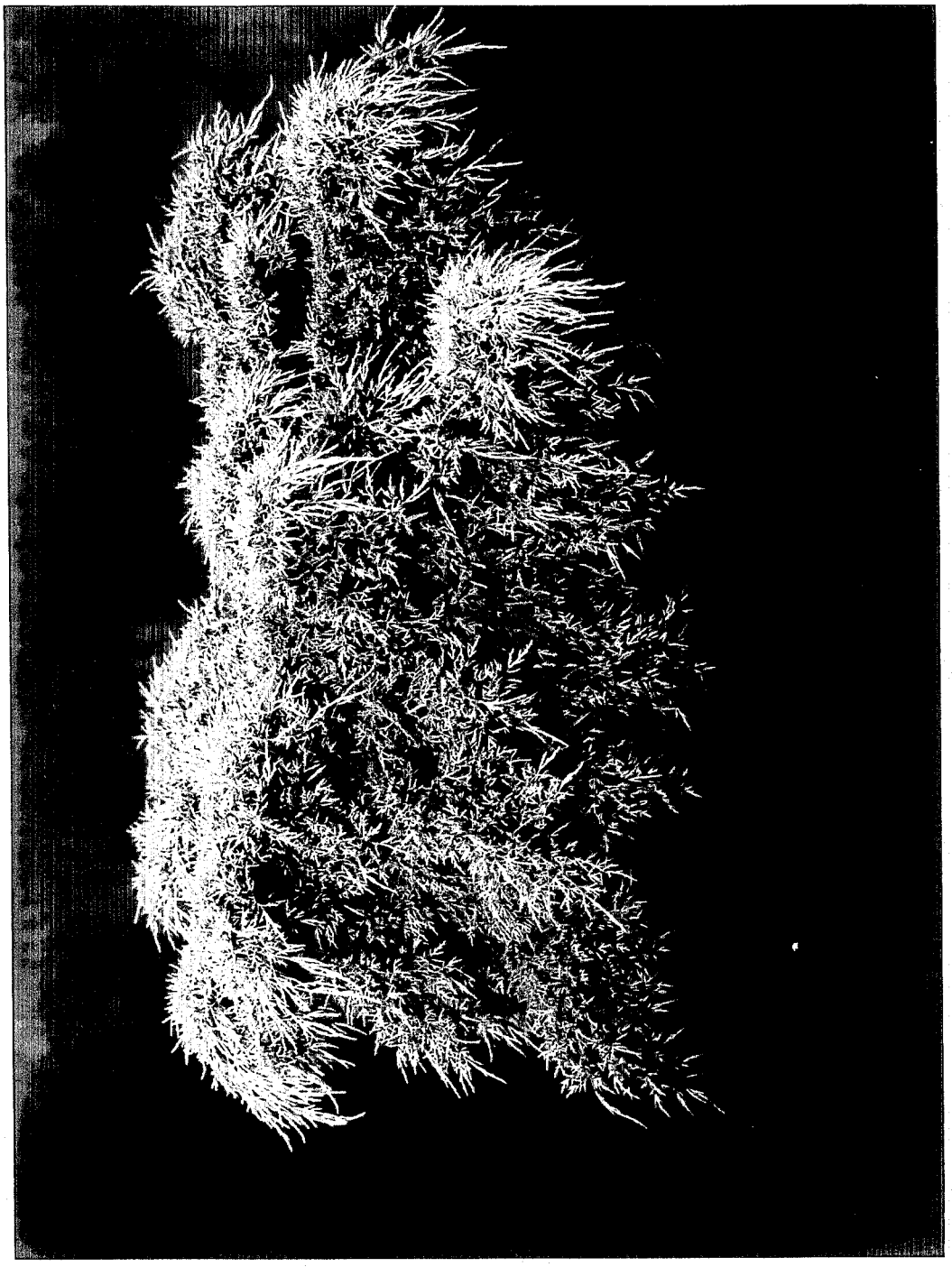

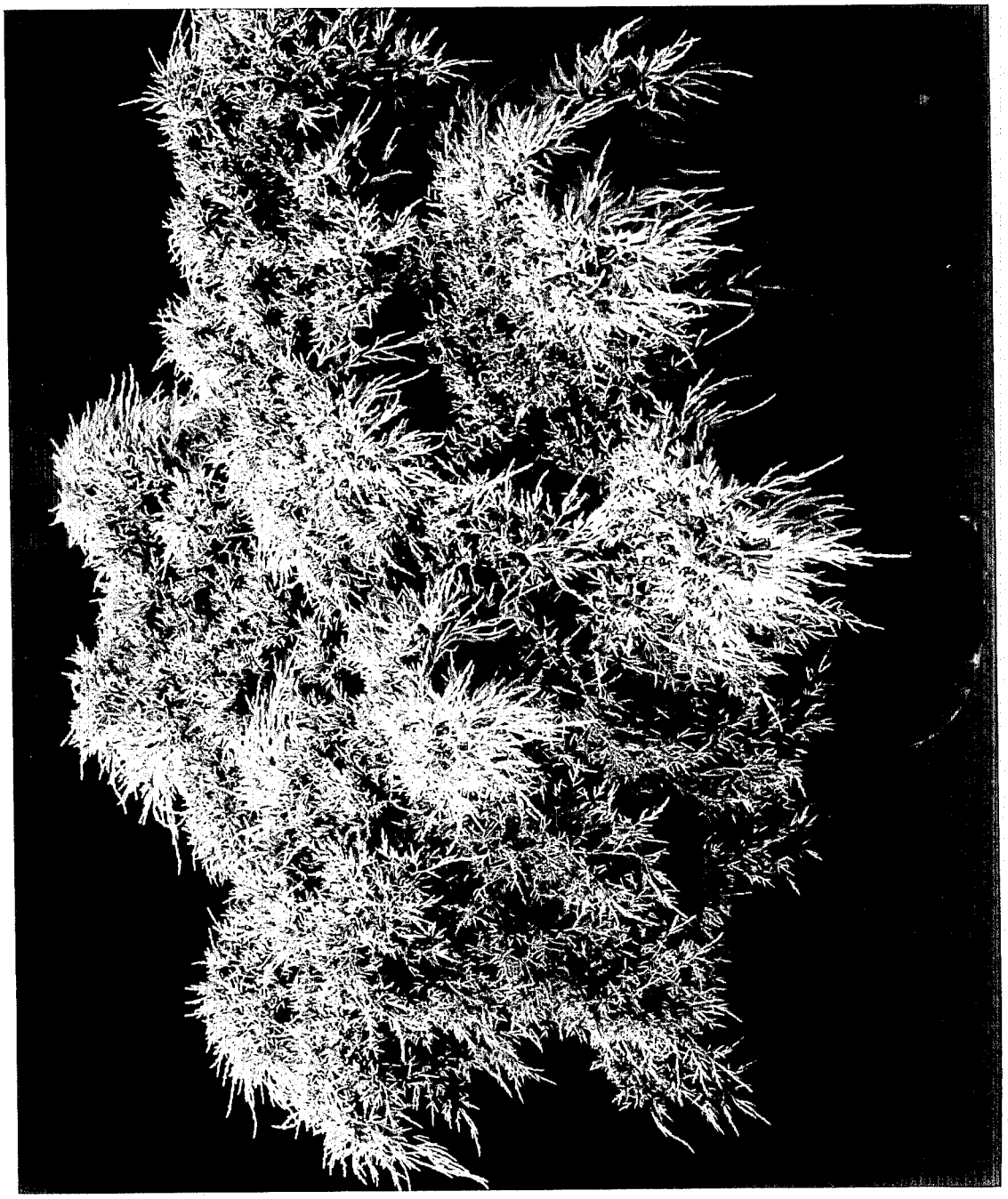

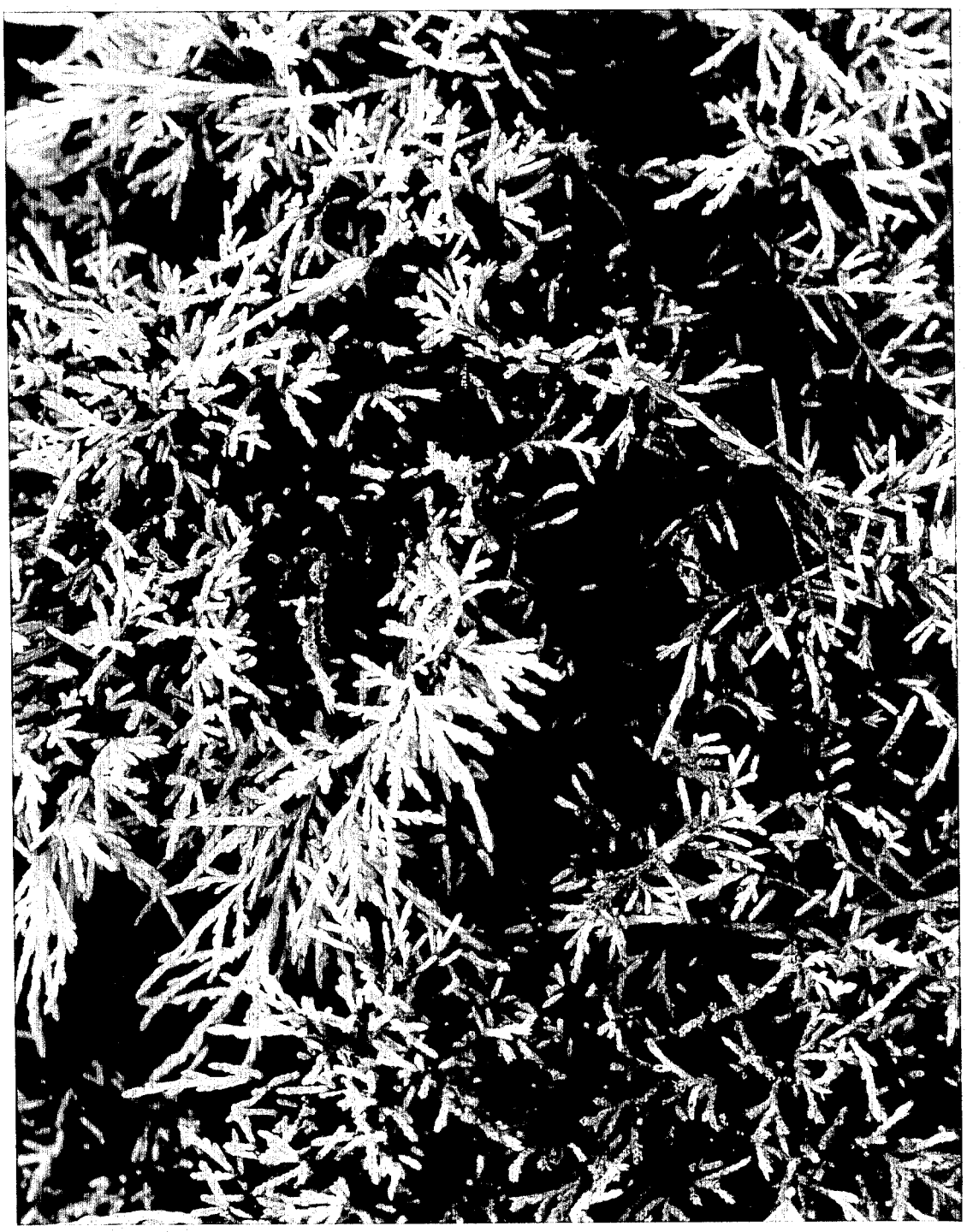

* * * * *